United States Patent [19]

Ohtaka et al.

[11] Patent Number: 5,153,012
[45] Date of Patent: Oct. 6, 1992

[54] PROCESS FOR PREPARING BEVERAGE CONTAINING BETA-CAROTENE

[76] Inventors: Hisaaki Ohtaka; Ryosei Sudo, both of World Foods Co., Ltd., 2-3 Hamuramachi Sakaecho 3, Nishitama-gun, Tokyo, Japan

[21] Appl. No.: 730,361

[22] Filed: Jul. 15, 1991

[30] Foreign Application Priority Data

Aug. 8, 1990 [JP] Japan .................................. 2-207988

[51] Int. Cl.$^5$ ............................................. A23L 1/302
[52] U.S. Cl. ........................................ 426/72; 426/73; 426/590
[58] Field of Search .................... 426/72, 73, 590, 599

[56] References Cited

U.S. PATENT DOCUMENTS

| | | | |
|---|---|---|---|
| 4,303,692 | 12/1981 | Gaull | 426/590 |
| 4,362,757 | 12/1982 | Chen | 426/599 |
| 4,732,773 | 3/1988 | Schott | 426/599 |
| 4,992,282 | 2/1991 | Mehansho | 426/73 |
| 5,023,095 | 6/1991 | Kirk | 426/72 |

*Primary Examiner*—Carolyn Paden
*Attorney, Agent, or Firm*—Jordan and Hamburg

[57] ABSTRACT

The present invention offers a method for preparing a β-carotene fortified beverage to prevent loss of the β-carotene therefrom, more particularly by the admixture of vitamins C, B$_2$ and E with β-carotene to stabilize the latter even under ambient conditions to minimize its loss from a beverage. The admixture of such anti-oxidative vitamins is designed in a well-balanced fashion for human nutrition.

5 Claims, 6 Drawing Sheets

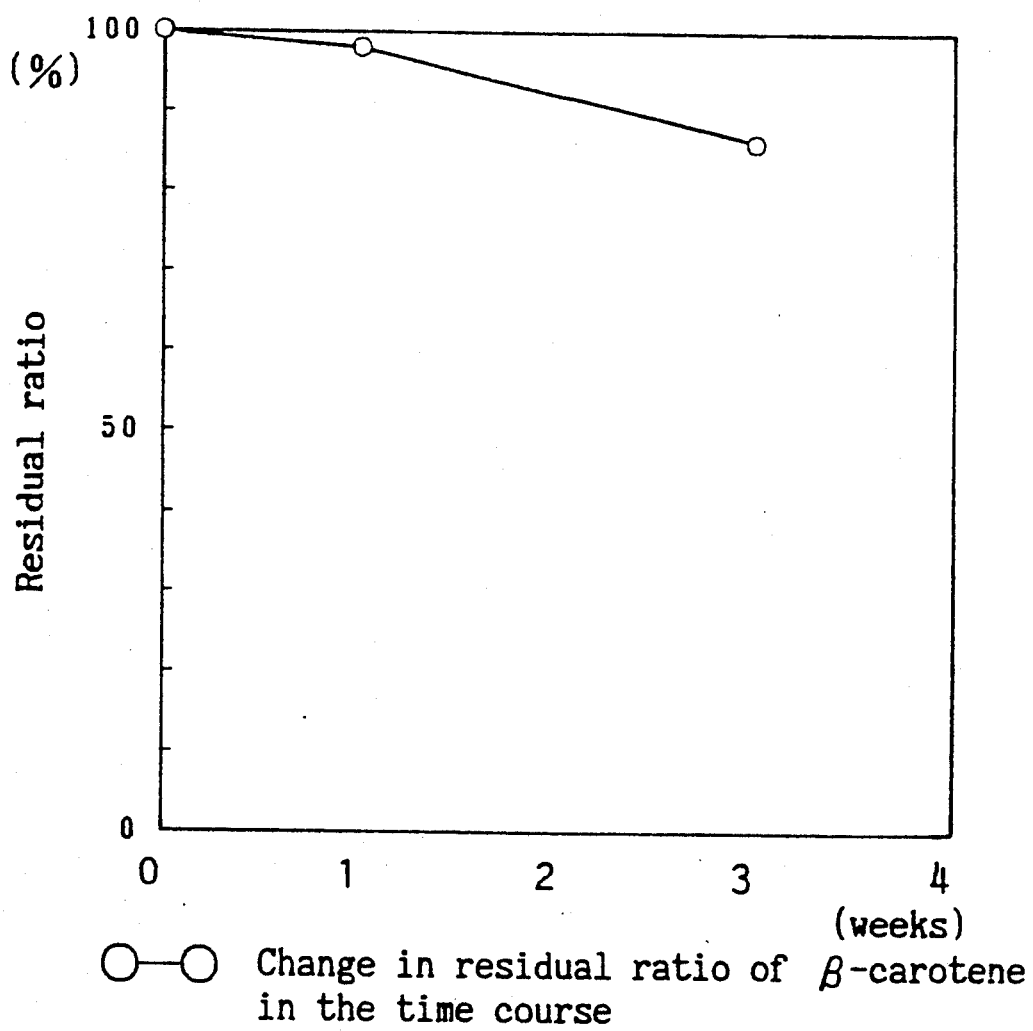

Change in β-carotene content in the beverage form(No.1) as solely fortified β-carotene stored up to 6 months.

▲—▲ Change in residual ratio of β-carotene in the time course stored at 10°C

■—■ Change in residual ratio of β-carotene in the time course stored at room temperature Change in β-carotene content in the beverage form (No.2) as both β-carotene and vitamin C fortified.

○—○ Change in residual ratio of β-carotene in the time course

●—● Change in residual ratio of vitamin C in the time course

Change in β-carotene content in the beverage form (No.3) as both β-carotene and vitamin E fortified.

○—○ Change in residual ratio of β-carotene in the time course

□—□ Change in residual ratio of vitamin E in the time course

Change in β-carotene content in the beverage form(No.4) as β-carotene and vitamins C and E as well as $B_2$.

○—○ Change in residual ratio of β-carotene in the time course

□—□ Change in residual ratio of vitamin E in the time course

●—● Change in residual ratio of vitamin C in the time course

△—△ Change in residual ratio of vitamin $B_2$ in the time course

Change in β-carotene content in the beverage form (No.4) as β-carotene and vitamins C and E as well as B₂ stored up to 6 months.

▲—▲ Change in residual ratio of β-carotene in the time course stored at 10°C

■—■ Change in residual ratio of β-carotene in the time course stored at room temperature

PROCESS FOR PREPARING BEVERAGE CONTAINING BETA-CAROTENE

BACKGROUND OF THE INVENTION

The present invention relates to a process for preparing a β-carotene fortified beverage in order to prevent the loss of β-carotene, more particularly by the admixture of vitamins C, $B_2$ and E with β-carotene to stabilize the latter even in ambient conditions to minimize its loss in the form of a beverage; in addition, the admixture of such anti-oxidative vitamins is designed in a well-balanced fashion for human nutrition.

β-carotene, now regarded as one of the primary functional components, has been considered to be provitamin A. However, recently its anti-oxidative property has drawn keen attention. Namely, β-carotene has been found to neutralize singlet oxygen which otherwise primes preoxidation of unsaturated fatty compounds. The reactive oxygen is generated from inspired oxygen and results in pathological aging with excess oxidative stress. The effective modulation of reactive oxygen may mean anti-aging. Therefore, there would be no surprise even though the constant intake of β-carotene has been shown to decrease the incidence of cancer, especially lung cancer, in epidemiological research. A lower content of serum β-carotene in a smoker might be due to ample free-radicals in the puffed fume. Therefore, intake of enough B-carotene constitutes a good preventive measure for the most serious kinds of cancer. Thus, it has long been sought to provide any easily accessible source of β-carotene in daily life.

A known beverage containing β-carotene includes carrot juice, as well as the mixture of carrot juice with other juice or juices, with or without fortification of its principal components, and is sold in can, bottle, carton, or plastic container. Even short surveys of this kind of product disclose very poor shelf-life, namely degrading color, flavor and taste over time. Especially, β-carotene is prone to discolor or oxidize by the irradiation of light (C.A. Pesek and J. J. Warthesen, J. Food Science 52 (3), 1987). Naturally, β-carotene is not only photo-sensitive but also reactive with oxygen, reflected by its structure, which makes construction of a long-life beverage containing β-carotene a matter of difficulty.

It is no wonder that so far no effective protection method has been invented for preparing such a β-carotene beverage. We extensively pursued the above aim, namely, how to stabilize the β-carotene moiety in a long-life beverage under ambient conditions without vitiating its flavor and have thus completed the present invention.

SUMMARY OF THE INVENTION

The present invention comprises a method of preparing a beverage containing β-carotene by coexisting three other anti-oxidative vitamins, namely vitamins C, $B_2$ and E, in order to prevent the loss of β-carotene; and a method of preparing a beverage containing β-carotene, in an amount of 3-20 mg per 100g of beverage, by coexisting vitamins C, 60–120 mg, E, 5–10 mg, and $B_2$, 0.5–1.0 mg, each amount per 100 g beverage.

BRIEF DESCRIPTION OF THE DRAWINGS

FIG. 1-1 shows the change in β-carotene content of a beverage Specimen No. 1 solely fortified with β-carotene.

FIG. 1-2 shows the change in β-carotene content of a beverage Specimen No. 1 solely fortified with β-carotene and stored up to 6 months.

FIG. 2 shows the change in β-carotene content of a beverage Specimen No. 2 fortified with both β-carotene and vitamin C.

FIG. 4-1 shows the change in β-carotene content of a beverage Specimen No. 4 fortified with β-carotene and vitamins C and E as well as $B_2$.

FIG. 4-2 shows the change in β-carotene content of a beverage Specimen No. 4 fortified with β-carotene and vitamins C and E as well as $B_2$ and stored up to 6 months.

Specimens No. 1 to No. 4 were prepared as described in Example below.

DESCRIPTION OF THE PREFERRED EMBODIMENTS

In the present invention, β-carotene may be derived from plants, carrots and green algae, by being crushed, squeezed, extracted and condensed into a puree or paste form, or chemically synthesized into a natural form from appropriate starting material. Other vitamins are procured from ordinary commercial sources.

In the present invention, the relative composition of the vitamins to supplement the beverage should be at least in the following range (per 100 g of beverage):

β-carotene: 3 to 20 mg
vitamin C: 60 to 120 mg
vitamin E: 2 to 10 mg
vitamin $B_2$: 0.3 to 1.2 mg The effects of the present invention are as follows:
1) In the presence of vitamin E, β-carotene can stay intact at the expense of vitamin E oxidation;
2) Then, oxidized vitamin E can be reduced by the vitamin C present and completely recycled for the protection of β-carotene; and
3) Vitamin $B_2$ can protect β-carotene from the irradiation of light with coexisting vitamin C by dispensing photons in the system.

EXAMPLE 1

The preparation of a β-carotene beverage was performed by the following steps:

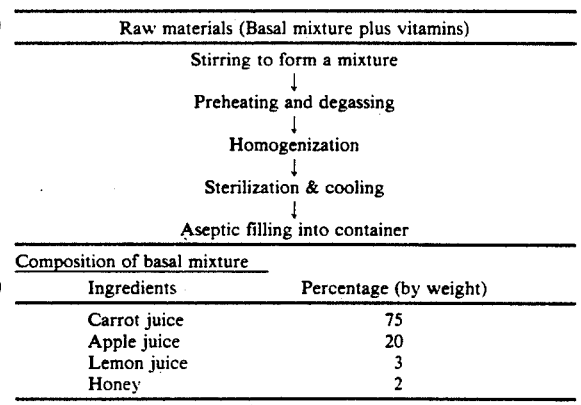

| Raw materials (Basal mixture plus vitamins) |
| --- |
| Stirring to form a mixture |
| ↓ |
| Preheating and degassing |
| ↓ |
| Homogenization |
| ↓ |
| Sterilization & cooling |
| ↓ |
| Aseptic filling into container |

| Composition of basal mixture | |
| --- | --- |
| Ingredients | Percentage (by weight) |
| Carrot juice | 75 |
| Apple juice | 20 |
| Lemon juice | 3 |
| Honey | 2 |

β-carotene to fortify as well as vitamins E, C and $B_2$ were added to the basal mixture stepwise to organize the following specimens No. 1–4 in aseptically filled brick packs (paper cartons). The vitamins were traced as to their contents after 4 weeks at 35° C. and 6 months at 10° and room temperature.

Specimen No. 1: Basal mixture plus β-carotene to fortify

Specimen No. 2: No. 1 plus vitamin C

Specimen No. 3: No. 1 plus vitamin E

Specimen No. 4: No. 1 plus vitamin C, E & $B_2$

Figures 1, 2:
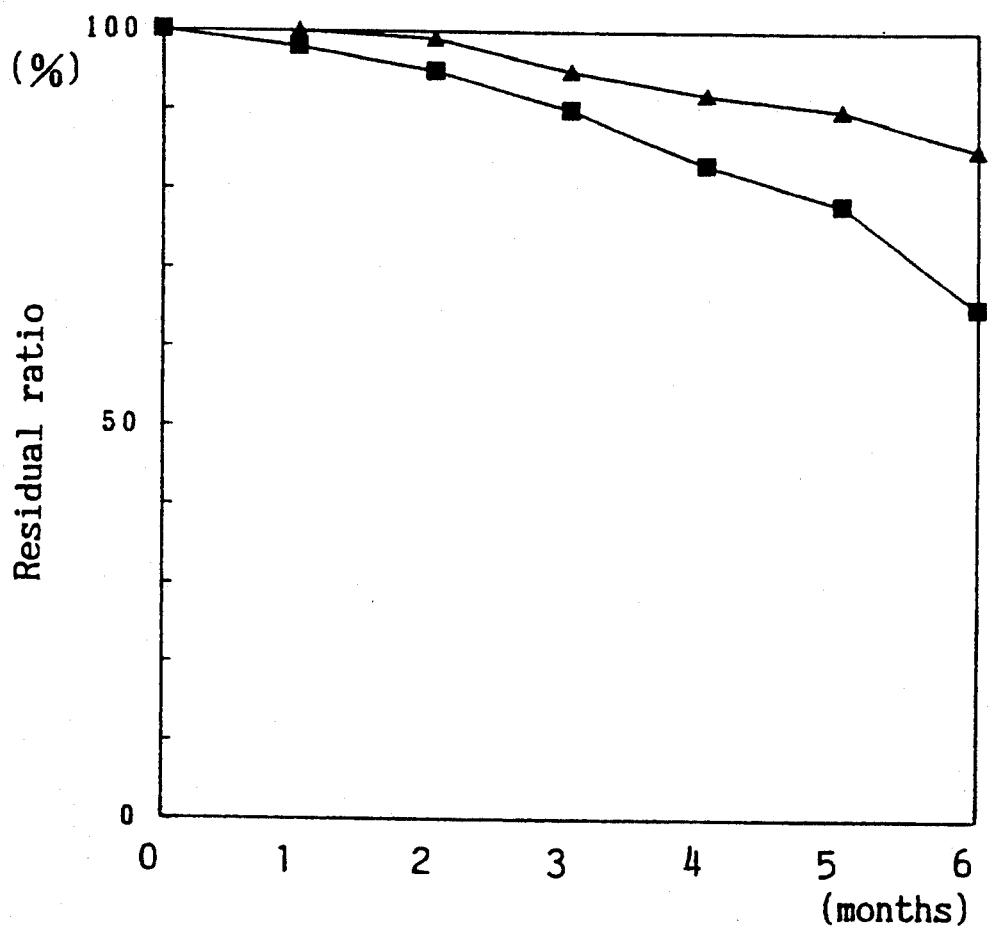
Figure 2:
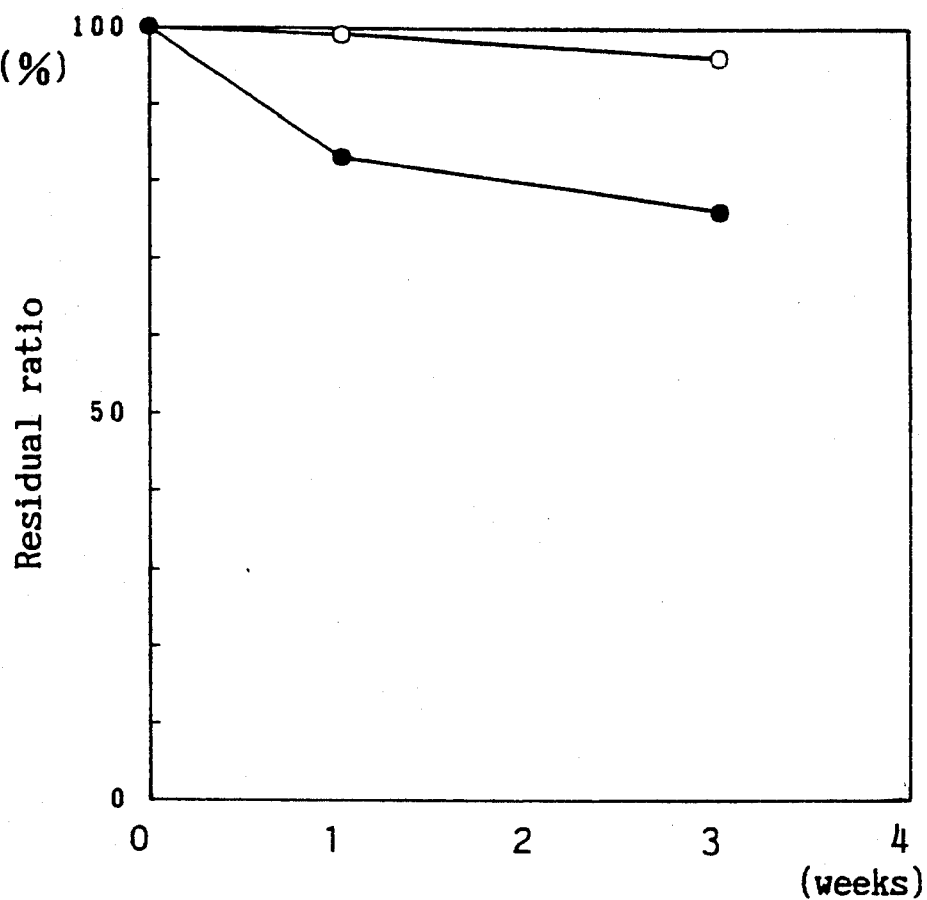
Figure 3:
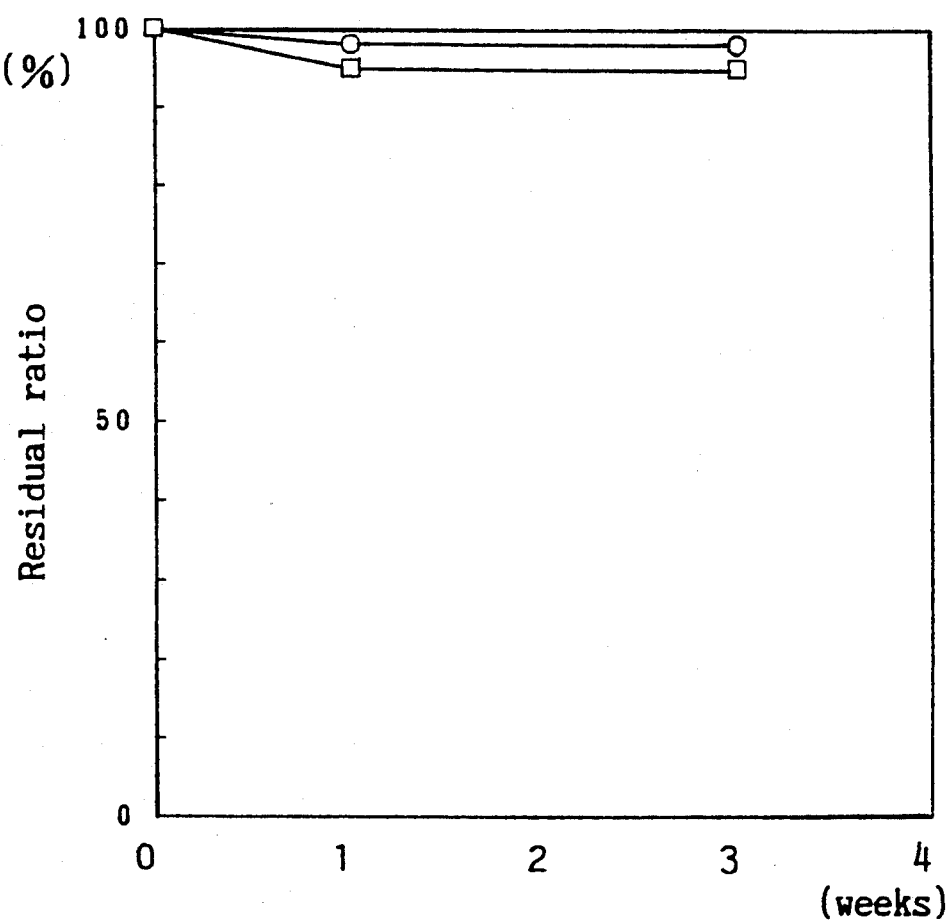
FIG. 3 shows the change in β-carotene content of a beverage Specimen No. 3 fortified with both β-carotene and vitamin E.
Figures 1, 4:
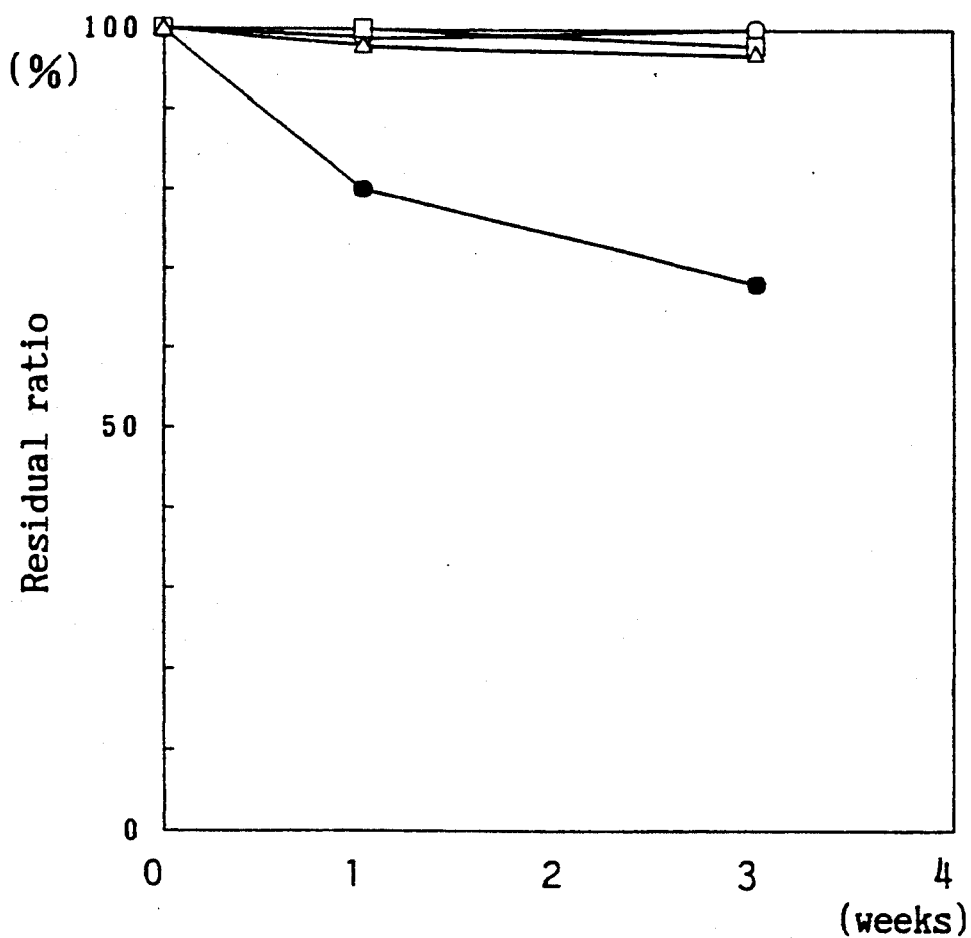
Figures 2, 4:
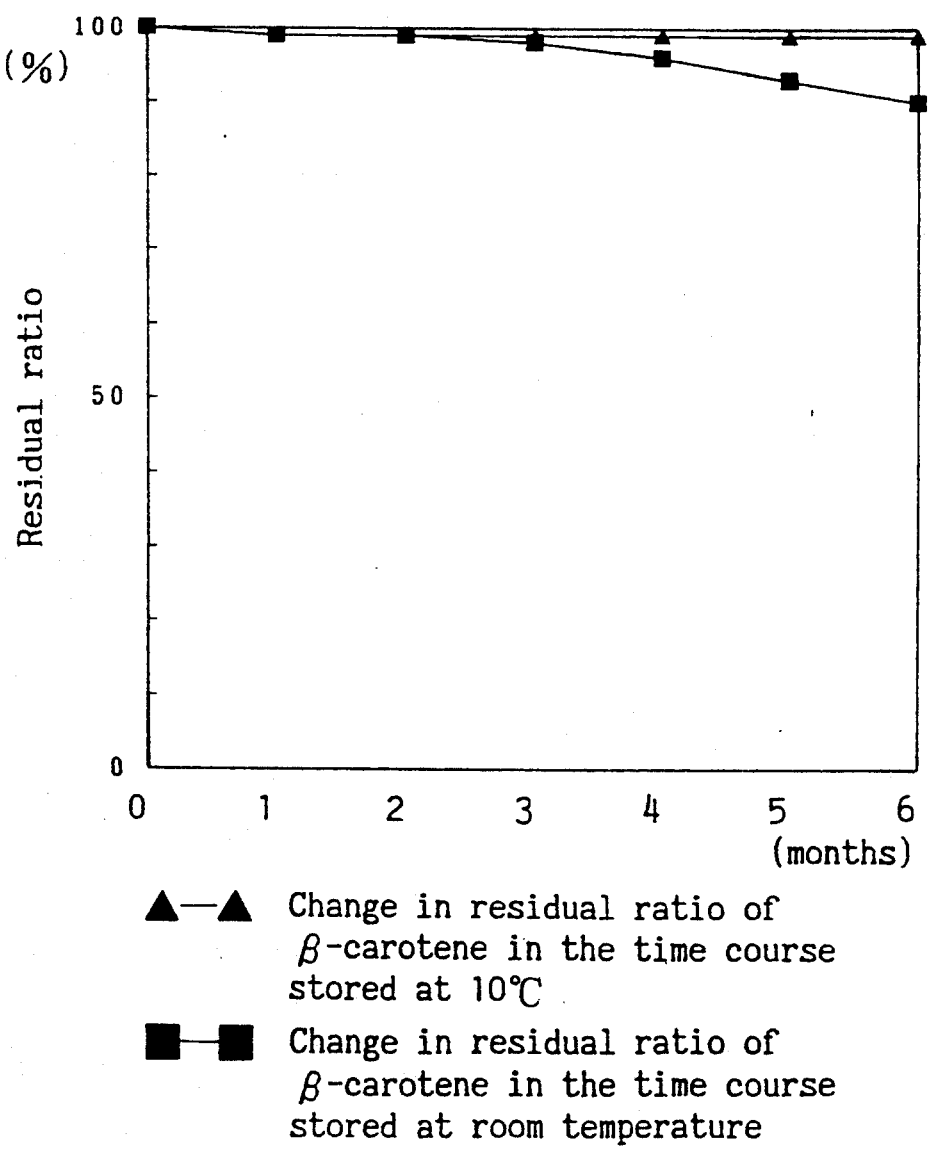

As shown in FIGS. 1-1 to 4-2, β-carotene stays reasonably intact in the presence of protective vitamins.

EXAMPLE 2

Specimen No. 5 was prepared as described above except for the addition of β-carotene with (No. 5-2) or without (No. 5-1) vitamins $B_2$ and C to the basal mixture and aseptically packed in a transparent glass bottle. The bottle was exposed to the irradiation of a fluorescent lamp (30W) for 2 weeks at room temperature. Table 1 shows changes in β-carotene and the coexisting vitamins, before and after 2 weeks of irradiation. The vitamin content was expressed in relative intensity with 100 signifying "before irradiation". Table 1 clearly shows the protective effect of vitamins C and $B_2$ for β-carotene under the irradiation of a fluorescent lamp.

TABLE 1

Changes in β-carotene content under irradiation with coexisting vitamins $B_2$ and C

| Specimen | Irradiation | β-carotene | vitamin $B_2$ | vitamin C |
|---|---|---|---|---|
| No. 5-1 | Before | 100 (%) | / | / |

TABLE 1-continued

Changes in β-carotene content under irradiation with coexisting vitamins $B_2$ and C

| Specimen | Irradiation | β-carotene | vitamin $B_2$ | vitamin C |
|---|---|---|---|---|
|  | After | 63 | / | / |
| No. 5-2 | Before | 100 | 100 | 100 |
|  | After | 91 | 51 | 10 |

The present invention makes possible a handsome intake of β-carotene, which is a necessary nutrient in modern life, without significant loss in storage and with a well-balanced assortment of anti-oxidative vitamins C, E and B2.

I claim:

1. A method for preparing a beverage containing β-carotene, comprising forming a beverage mixture, and adding to said beverage mixture β-carotene and effective amounts of anti-oxidative vitamin C, vitamin $B_2$ and vitamin E to minimize the loss of β-carotene from the beverage over time.

2. A method according to claim 1, wherein said β-carotene, vitamin C, vitamin $B_2$ and vitamin E are added to said beverage mixture sequentially.

3. A method according to claim 1, wherein said beverage mixture is a basal mixture.

4. A method according to claim 1, wherein said effective amounts, per 100 g of beverage, are 60 to 120 mg of vitamin c, 2 to 10 mg of vitamin E, and 0.3 to 1.2 mg of vitamin $B_2$, and said β-carotene is added in an amount of 3 to 20 mg per 100 g of beverage.

5. A method according to claim 1, wherein said effective amounts, per 100 g of beverage, are 5 to 10 mg of vitamin E and 0.5 to 1.0 mg of vitamin $B_2$.

* * * * *